US005972602A

United States Patent [19]
Hyland et al.

[11] Patent Number: 5,972,602
[45] Date of Patent: Oct. 26, 1999

[54] QUANTITATIVE PCR-BASED METHOD OF GENE DETECTION

[75] Inventors: Catherine Hyland, Camp Hill; Lindsay Colin Wolter, Holland Park; Allan Saul, The Gap, all of Australia

[73] Assignees: Australian Red Cross Society, Brisbane, Queensland; The Council of the Queensland Institute of Medical Research, Herston, Queensland, both of Australia

[21] Appl. No.: 08/607,631

[22] Filed: Feb. 27, 1996

Related U.S. Application Data

[63] Continuation of application No. PCT/AU95/00506, Aug. 29, 1994.

[30] Foreign Application Priority Data

Aug. 27, 1993 [AU] Australia ............................... PM 0859

[51] Int. Cl.$^6$ ............................. C12Q 1/68; C07H 21/02; C07H 21/04; C12N 15/00
[52] U.S. Cl. ........................... 435/6; 536/23.1; 536/24.3; 935/76; 935/77; 935/78
[58] Field of Search ............................... 435/6, 91.2, 810, 435/270; 536/22.1, 23.1, 24.33, 23.5; 935/77, 78

[56] References Cited

U.S. PATENT DOCUMENTS

| 5,219,727 | 6/1993 | Wang et al. ................................. 435/6 |
| 5,496,699 | 3/1996 | Sorenson et al. ........................... 435/6 |
| 5,639,611 | 6/1997 | Wallace et al. ............................. 435/6 |

FOREIGN PATENT DOCUMENTS

| 90 12840 | 4/1992 | France . |
| 93/18177 | 9/1993 | WIPO . |
| 93/18178 | 9/1993 | WIPO . |
| 93/22456 | 11/1993 | WIPO . |

OTHER PUBLICATIONS

Lo et al., "Prenatal Determination of Fetal RhD Status by Analysis of Peripheral Blood of Rehesus Negative Mothers" *The Lancet*, vol. 341:1147–1148, (1993).
Arce et al., "Molecular Cloning of RhD cDNA Derived From A Gene Present In RhD–Positive, But Not RhD–Negative Individuals", *Blood*, vol. 82(2):651–655, (1993).
Le Van Kim, "Molecular Cloning And Primary Structure Of The Human Blood Group RhD Polypeptide", *Proc. Natl. Acad. Sci. USA*, vol. 89:10925–10929.
Wolter et al., "Rhesus D Genotyping Using Polymerase Chain Reaction", *Blood*, vol. 82(5):1682–1683, (1993).
Colin et al., "Genetic Basis of the RhD–Positive And RhD–Negative Blood Group Polymorphism As Determined by Southern Analysis", *Blood*, vol. 78(10):2747–2752, (1991).
Derwent WPAT online Abstract Accession No. 92–194019/24, FR 2668162–A1 (Lab Eurobio), Oct. 17, 1990.
Bennett et al., "Prenatal Determination of Fetal RhD Type By DNA Amplification", *The New England Journal of Medicine*, vol. 329(9):607–610, (1993).
Ugozzoli et al., Allele–Specific Polymerase Chain Reaction. Methods 2 (1) : 42–48 (1991).
Okayama et al., Rapid, non–radoioactive detection of mutations in the human genome by allele–specific amplification. J. of Laboratory and Clinical Medicine 114(2) : 105–113 (1989).

*Primary Examiner*—Ardin H. Marschel
*Assistant Examiner*—Ethan Whisenant
*Attorney, Agent, or Firm*—Foley & Lardner

[57] ABSTRACT

A method of detecting a gene and quantifying its copy number using a PCR based assay is described. A set (i.e. three primers) of PCR primers is used in a single reaction wherein the first primer is specific for a first gene and the second primer is specific for a second gene which second gene is closely related to the first gene, while the third primer is common to both the first and second genes. From the results obtained the presence or absence of the second gene can be determined, as well as, its copy number.

10 Claims, 1 Drawing Sheet

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 12 base pairs
      (B) TYPE: nucleic acid
      (C) STRANDEDNESS: single
      (D) TOPOLOGY: linear (xi) SEQUENCE DESCRIPTION: SEQ ID NO:1:

GCATGHCTCA TT                                                      12

(2) INFORMATION FOR SEQ ID NO:2:

(i) SEQUENCE CHARACTERISTICS:
      (A) LENGTH: 32 base pairs
      (B) TYPE: nucleic acid
      (C) STRANDEDNESS: single
      (D) TOPOLOGY: linear (xi) SEQUENCE DESCRIPTION: SEQ ID NO:2:

GATTACGAAT TCGTAACCGA GTGCTGGGGA TT                      32

(2) INFORMATION FOR SEQ ID NO:3:

(i) SEQUENCE CHARACTERISTICS:
      (A) LENGTH: 33 base pairs
      (B) TYPE: nucleic acid
      (C) STRANDEDNESS: single
      (D) TOPOLOGY: linear (xi) SEQUENCE DESCRIPTION: SEQ ID NO:3:

TACCAGATTA CGAATTCATG CCATTGCCGG CTC                    33

(2) INFORMATION FOR SEQ ID NO:4:

(i) SEQUENCE CHARACTERISTICS:
      (A) LENGTH: 29 base pairs
      (B) TYPE: nucleic acid
      (C) STRANDEDNESS: single
      (D) TOPOLOGY: linear (xi) SEQUENCE DESCRIPTION: SEQ ID NO:4:

GATTACGAAT TCCATTGCCG TTCCAGACA                        29

QUANTITATIVE PCR-BASED METHOD OF GENE DETECTION

This application is a continuation of PCT/AU95/00506 filed Aug. 29 1994.

FIELD OF INVENTION

THIS INVENTION relates to detection of genes and in particular detention of one of a number of closely related genes which usually will have their respective sequences already determined, although this is not essential.

The invention may be primarily directed at genes which are present in human cells although this is not the only application of the invention and thus the invention may be directed to genes present in animal cells or in plant cells.

The invention however has particular relevance to detection of rhesus (Rh) D blood group antigens and thus may be utilised for rhesus D genotyping.

BACKGROUND ART

The rhesus blood group antigens are clinically important because of their highly immunogenic nature. Specifically they are central in the pathogenesis of Rh haemolytic disease of the new born (HDN) and some autoimmune haemolytic anemias. Furthermore in blood transfusion it is important to avoid immunisation of Rh-negative recipients, particularly women, with Rh-positive blood and to avoid transfusion of immunised patients with Rh-incompatible blood products. There are five most commonly typed Rh antigens: C/c, E/e and the D antigen which is the most immunogenic, defining an individual as Rh-positive or Rh-negative. Previously it was hypothesised that RhD may have an alternative allelic gene which was designated (d); however, Southern analysis has since shown that RhD negative phenotypes result from the absence of RhD genes that code for the D antigen as described in Colin et al Blood 78:2747 (1991). In other words RhD-positive individuals have either one or two RhD genes per cell and RhD-negative individuals have no RhD genes at all.

RhD typing was initially performed by agglutination with human polyclonal anti-D sera but has recently progressed to agglutination with IgM and/or blends or IgM and IgG anti-D monoclonal antibodies. However, even these monoclonal antibodies may not detect some weak RhD antigens and RhD variants. Additionally these serological techniques only allow a probable RhD genotype (one or two D genes) to be assigned based on Rh phenotype and available population statistical data. Often unambiguous RhD genotypic information is required such as in the case of prenatal counselling of Rh-negative mothers previously immunised with an Rh-positive child.

Reference may also be made to Lo et al. Vol 341 1147–1148 of the Lancet (1993) wherein a prenatal determination of fetal RhD status by analysis of peripheral blood of rhesus negative mothers was carried out. In this reference the authors utilised firstly the sequence of the recently cloned RhD gene (Le Van Kim et al. Proc Natl Acad. Sci USA (1992) 89 10925–29), and secondly the observation that RhD negative individuals lack this gene (Colin et al. Blood 78 2747 1991). Lo et al therefore designated a PCR assay to detect RhD DNA sequences from a RhD-positive fetus by amplification from the peripheral blood of RhD-negative mothers.

In the Lo et al. assay the controls utilised were a 1 in $10^5$ dilution of 1 μg homozygous RhD-positive DNA in 5 μg RhD-negative male DNA as a positive control and water as a negative control. The other samples assayed were clinical samples from patients as well as 5 μg RhD-negative male DNA. The marker utilised was pBR322 DNA digested with HaeIII.

In the Lo et al. PCR assay PCR primers were designed to amplify regions outside one coding sequence for the D gene at the 3' end. They did this because the Rh CE gene and D genes are very closely related. They therefore chose the 3' non coding region of the D gene which differs from the CE gene. They therefore did not amplify the CE gene at all. In the PCR assay PCR products were analysed by agarose gel electrophoresis. However, this PCR assay could only indicate the presence or absence of the RhD gene in the sample tested and could not be utilised for quantifying the number of RhD genes present (ie. one or two genes). The inability to quantify the number or dosage of RhD genes present means that a true RhD genotype of an individual could not be assigned.

Reference also may be made to Arce et. al. Blood 82 651–655 (1993) which refers to molecular cloning of RhD cDNA derived from a gene present in RhD positive, but not RhD negative individuals as well as Bennett et al. The New England Journal of Medicine, Aug. 26 (1993) 607–610 which refers to prenatal determination of fetal RhD type by DNA amplification. Both these references identify the D gene but do not give a D gene dosage unlike the present invention.

In the Bennett et al. reference two pairs of primers are produced wherein a first pair of primers amplify a 136 bp region common to the RhCcEe and RhD genes (i.e. exon 7) and the second pair of primers amplify a 186 bp region specific to the 3' untranslated sequence (exon 10) of the RhD gene. The two amplification reactions are performed in the same tube. Only the 136 bp product is amplified from RhD negative DNA whereas both the 136 bp and 186 bp products are amplified from RhD positive DNA.

The Arce et al. reference amplifies a region of the D gene known as "exon 4 to 5" by experiments carried out by the inventor(s). It has also been established that the exon 10 method gives more false positives than exon 7. It has also been established that PCR of exon 4 to 5 is also subject to false positives and is hard to perform.

SUMMARY OF THE INVENTION

It therefore is an object of the invention to provide a process and test kit for detection of one or a number of closely related genes which is efficient and which may alleviate to at least a certain extent the disadvantages described above in relation to conventional detection of RhD antigens.

The invention is therefore relevant to a situation involving closely related genes involving a first gene which is normally found in a copy number of at least 1 per cell and a second gene which may be present in a copy number of 0, 1, 2 or more per cell and it is desired to not only detect the presence of the second gene in human, animal and plant cells but also quantify the presence of the second gene in copy number. In the specific example referred to above the CcEe gene is normally present in humans in a copy number of 2 per cell and the RhD gene may be present in a copy number of 0, 1 or 2 per cell.

In another example D variant genes may usually be present in a copy number of 0 or 1 per cell and therefore the invention may he applicable to detection and quantification in copy number of either the RhD gene or RhD variant gene using the CcEe gene as an appropriate control.

While the invention has particular relevance to genes which have had their nucleotide sequence already determined it also has relevance to genes which have yet to have their nucleotide sequence determined provided that such genes will be found to be closely related in nucleotide sequence at a later date.

The process of the invention may therefore a process for quantifying the presence in copy number of one of a number of closely related genes which includes the steps of:

(i) carrying out a PCR assay with one or more test samples from a human, animal or plant cell extract wherein the or each sample includes a DNA call extract having (a) a first gene always present in such DNA cell extract at a fixed copy number of 1 or more per cell, and (b) a second gene closely related to the first gene but usually present in the DNA cell extract in a copy number of 0, 1, 2 or more per cell together with a first primer specific for said first gene, a second primer specific for said second gene and a third primer common to both the first gene and the second gene to produce a first PCR product corresponding to the first gene which first PCR product generates a first signal and, if the second gene is present, a second PCR product corresponding to the second gene which second PCR product generates a second signal; and (ii) quantifying the presence in copy number of the second gene in the or each test sample by comparison of the first signal with the second signal.

The process of the invention may also be directed to the detection and quantification in copy number of one of a number of closely related genes in cell extracts and thus include detection and quantification in copy number of the second gene or another gene closely related to tire second gene (which may be a mutation of the second gene).

In specific reference to RhD genotyping the first gene may correspond to the CcEe gene (which is normally present in a copy number of 2 per cell) and the second gene may correspond to the RhD gene or RhD gene variants. in copy number of the second gene or another gene closely related to the second gone (which may be a mutation of the second gene).

In specific reference to RhD genotyping the first gene may correspond to the CcEe gene (which is5 normally present in a copy number of 2 per cell) and the second gene may correspond to the RhD gene or RhD gene variants.

Figure 1:
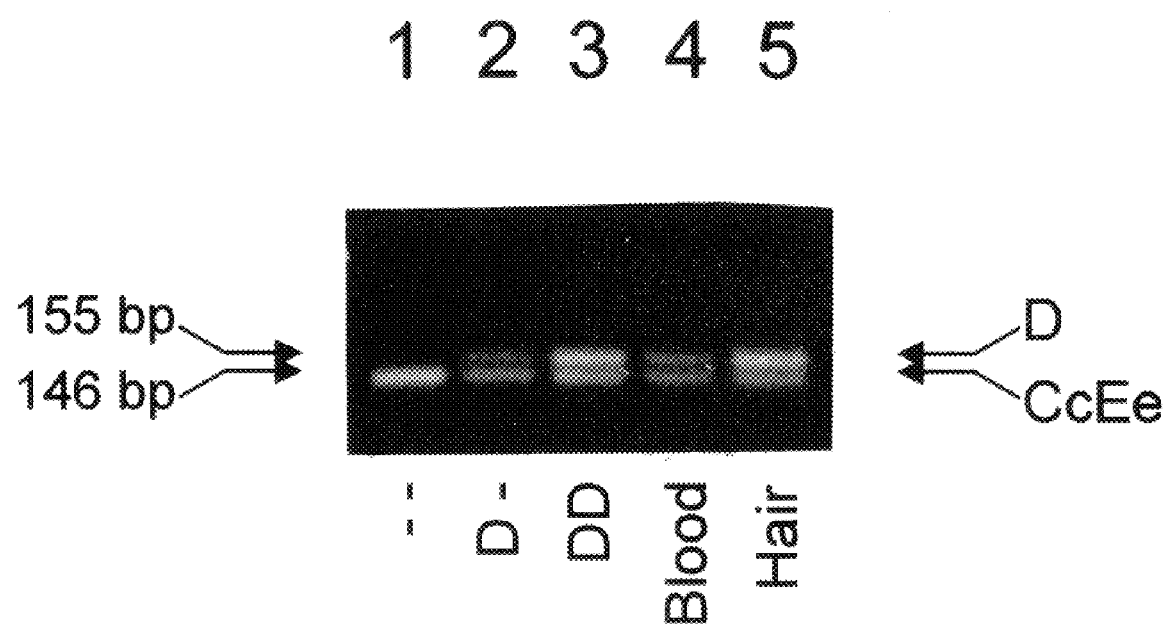
FIG. 1 shows a typical PCT result according to the process of the invention.

The PCR assay may be carried out using as an enzyme component a source of thermostable DNA polymerase suitably comprising Taq DNA polymerase which may be the native enzyme purified from *Thermus aqueticus* and/or a genetically engineered form of the enzyme synthesised in *E. coli* sold under the trade mark AMPLITAQ. Other commercially available polymerase enzymes include Taq polymerases marketed by Promega or Pharmacia. Another thermostable DNA polymerase that could be used is Tth DNA polymerase obtainable from *Thermus thermophilus*. Concentration ranges of the polymerase may range from 0.5–5.0 units per 100 μl of reaction mixture.

Deoxyribonucleotide triphosphates comprising dATP, dCTP, dGTP and dTTP (i.e. dNTPs) can be utilised in the assay with it being realised that dGTP may be substituted with 7-deaza-2'-deoxy GTP and 7-deaza-2'-deoxy ATP can be substituted for dATP. It will also be appreciated that 2'-deoxy ITP can be substituted for any dNTP. The four dinucleotides may be present in a PCR reaction mixture at a concentration of 20–200 μM and at a pH of about 7.0.

Any suitable biological buffer may also be utilised in the reaction mixture such as Tris-HCl, or Tricine which can provide a pH in the range of 7.4–8.8. Tris-HCl may provide a pH of 8.3–8.8 at 20° C. and Tricine may provide a pH of 8.4. The concentration of buffer may be 10–50 mM in the case of Tris-HCl and around 300 mM in the case of Tricine.

The buffer may also comprise a source of $Mg^{--}$ such as $MgCl_2$ which may affect (i) primer annealing (ii) strand dissociation temperatures of both template and PCR product, (iii) product specificity, (iv) formation of primer-dimer artifacts and (v) enzyme activity and fidelity. Taq polymerase may require free $Mg^{++}$ on top of that bound by template DNA, primers and dNTPs. Accordingly the PCR mixture may contain 0.5–2.5 mM $Mg^{++}$ over the total dNTP concentration.

The buffer may also include KCl in a concentration of up to 50 mM to facilitate primer annealing.

Another optional component may be B-mercaptoethanol in a concentration of 50 mM.

Gelatin or bovine serum albumin (BSA) may also be present in a concentration range of 0.01–0.1%.

Nonionic detergents such as Tween 20, Triton X-100, or Laureth 12 in a concentration range of 0.03 to 0.1% may also be added to help stabilize the enzyme.

The primer components may be present in the PCR reaction mixture at a concentration of between 0.1 and 0.5 μM. The primer length may to between 18–40 nucleotides in length and having 50–60% G and C composition.

In the choice of primer it is preferable to have exactly matching bases at the 3' end of the primer but this requirement decreases to being relatively insignificant at the 5' end (this is described in Nucleic Acids Research 19 3058). The preferred primers utilised in thus invention have a restriction site and m13 sequence added to the 5' end.

The published RhD and Rh CcEe sequence data referred to in Le Van Kim et al. Proc Natl Acad Sci USA 89 10925–10929 (1992) and Cherif-Zehar at al. Procl Natl Acad Sci 87 6243 (1990) differs by only 44 bases. Using sequence differences in exon 7 specific primers were therefore designed for the PCR assay described hereinafter.

In the reaction conditions applicable to PCR assay, an initial denaturation step may be carried out between 90–100° C., a subsequent annealing step carried out between 40–60° C. and a final extension step may be carried out between 70–75° C. Alternatively the annealing step and extension step may be combined if considered appropriate.

However it will be appreciated that other primers along other regions of the gene could be designed so as to distinguish RhD from Rh CcEe where there is at least one consecutive mismatch in the RhD/CcEe sequence.

In this regard there are two ways of making different size bands which may be detected for example in gel electrophoresis by making one of the gene specific primers longer than the other or by designing one primer further from the common primer. In the present invention either of these situations could apply.

In accordance with the present invention however the PCR assay is designed so that the D and CE amplified fragments are distinguishable and this may be achieved by designing either the forward or reverse primers such that one primer is common (e.g. forward) to both genes and one is unique for either D or CE.

The unique primers may also be juxtapositioned at slightly different positions along the D and CE gene respectively to give different size products. In addition, to further enhance the size difference between the two products, one primer may be artificially extended for example by the addition of extra M13 sequences.

In an alternative situation instead of distinguishing between the D and CE genes using a size difference as described above it may be possible to tag the primers unique for D and CE with different markers which would give a fluorometric or colourmetric end point detection system. Suitable markers may be fluorescence markers or enzyme markers such as horse radish peroxidase or the biotin/avidin system. These markers may be adaptable to either the CAPTAGENE system as herein described or the Dot Blot Matrix System.

In the PCR assay the concentration of the common primer is preferably less than the respective concentrations of the gene specific primers.

It will also be appreciated that the common primer may be either a forward or reverse primer with the gene specific primers being both reverse or forward respectively.

In the present invention the PCR amplified exon 7 as this exon contained the most divergence between D and CE. It was therefore easier to design primers to this region. However, it is clearly within the scope of the invention to amplify other exons and exon/intron boundary areas to achieve a similar result. For example the ocher exons and exon/intron boundary areas may be amplified as either additional controls or to give more information about D variants.

In this regard the invention may also be applicable to not only the known sequence for D, but also D variants when the sequences of the D variants become known. In this aspect of the invention primers may then be designed specific for these variants and an analogous PCR assay could be utilised to determine D variant classification relevant to a particular individual.

Detection of DNA products within the scope of this invention can be achieves using a number of commercial systems. They mostly rely upon attaching a protein or protein binding site sequence to the end of a primer and by using either a bound antibody (specific for the bound protein) or protein (that binds to the protein binding site) to select amplified DNA fragments. Binding can be done in any vessel or material that can attach DNA or proteins. Most methods deal with detection of only one products however by suitably modifying such methods two or more DNA products could be detected. For example detection of DNA products could be carried out using the AMRAD CAPTAGENE system which is a commercially available detection system for amplifying specific sequences of DNA using microtitre plate technology. This system requires DNA amplification using oligonucleotide primers one of which is biotinylated and the second of which incorporates a specific 12 bp recognition sequence (SEQ ID NO: 1) 5'-GCATGHCTCATT for a double stranded DNA binding protein GCN4 which is a GST fusion protein. Such modifications may include (1) using the GCN4 binding sequence within the common primer—this will allow both D and CcEc fragments to be bound to the wells of the microtitre plate; and (2) using different proteins/dyes for each gene specific primer so that detection can be performed quantitatively for each gene fragment. With visible detection, one could use biotin attached to one primer (to be detected with avidin-HRP) and attach another protein/enzyme substrate to the other primer with its own antibody/enzyme detection system and react these enzymes sequentially reading values with a spectrophotometer. If dyes having different fluorescence profiles were attached to individual primers such as the TOTO-1/YOYO-1 and TOTO-3/YOYO-3 fluorescent probes obtained from Molecular Probes Inc., both bands could be read with a UV spectrophotometer (Millipore CytoFluor 235 fluorescence plate reader) by simply changing wavelength. Molecular Probes Inc. also supply dyes having visible absorbance that could be used in a similar way.

It will also be appreciated that electrophoresis gels such agarose gel electrophoresis of polyacrylamide gel electrophoresis may be utilised for detection of DNA products.

The present invention also extends to the use of one or more external reference standards in step (i) of the process each of which comprises a DNA cell extract indicating the presence of said first gene in a copy number of at least 1 per cell and indicating the presence of the second gene in the copy number of 0, 1, 2 or more per cell wherein the number of reference standards corresponds to the variation in copy number of the second gene.

Preferably, there is a plurality of reference standards used in step (i) of the process including:

(a) said first gene and said second gene in a copy number of 0;

(b) said first gene and said second gene in a copy number of 1; and (c) said first gene and said second gene in a copy number of 2.

The DNA samples utilised for the PCR assay are suitably purified by any suitable means prior to incorporation in the PCR reaction mix. Any method which purifies DNA from a liquid may be utilised such as commercial purification systems e.g. GENECLEAN (B10101) or MAGIC MINI-PREPS available from Promega. A salting out method may also be used. Preferably when obtaining a quantitative assessment of the number of gene copies per cell (ie. 0, 1 or 2) the DNA sample is purified. Human tissue can also be utilised such as whole blood containing leucocytes or hair follicle tissue. Again such tissue samples are preferably purified for quantitative assessment although this may not be necessary in relation to qualitative assessment.

EXPERIMENTAL

The published Rh D and CcEe gene sequences differ by only 44 bases. Using sequence differences in exon 7, a forward primer (SEQ ID NO: 2) (5'-GATTACGAATTCGTAACCGAGTGCTGGGGATT-3') was designed common to both genes, starting at nucleotide position 947, and reverse primers (SEQ ID NO: 3) (5'-TACCAGATTACGAATTCATGCCATTGCCGGTC-3' and (SEQ ID NO: 4) 5'-GATTACGAATTCCATTGCCGTTCCAGACA-3'), specific for D starting at nucleotide 1058 and CcEe starting at nucleotide 1053 respectively were also designed. These PCR primers give 155-bp and 146-bp fragments for the D and CcEe genes allowing these products to be distinguished by agarose gel electrophoresis.

The PCR reaction consisted of 50 mmol/L KCl, 10 mmol/L Tris-HCl (pH 9.0 at 25° C.), 1% Triton X-100, 2 mmol/L $MgCl_2$, 0.2 mmol/L each of dATP, dCTP, dGTP, and dTTP in a volume of 50 $\mu$L $H_2O$ containing 80 ng forward primer, 120 ng of each reverse primer, 2.5 U Taq polymerase (Promega, Madison, Wis.) and 50 ng human genomic DNA. It is important that the common forward primer be in reaction limiting amounts for a quantitative result. Standard polymerase chain reaction (PCR) conditions were one cycle of 94° C. for 3 minutes, 56° C. for 2 minutes, 72° C. for 2 minutes, and 35 cycles of 95° C. for 30 seconds, 65° C. for 1 minute and a final extension of 72° C. for 3 minutes.

The PCR results in FIG. 1 show either one PCR product (Rh neg) or two PCR products (Rh pos). The CcEe gene product is the lower band (146 bp) and the D gene product is the upper band (155 bp). The number of copies of the D gene can be determined by comparing the intensity of the two bands. The CcEe gene that has two gene copies per cell acts as an internal PCR control (Rh neg; lane 1).

Therefore, a half intensity of the D band compared with CcEe band predicts a single D gene, a heterozygous carrier of D (lane 2). Likewise, an equal or greater intensity of D band compared with CcEe band (lane 3) indicates two D gene copies, a homozygous carrier for D. In practice, the D band intensity of a homozygote consistently appears slightly stronger than the CcEe band probably because of better priming of the D gene-specific primer. Results were also obtained using whole blood (lane 4) and hair follicles (lane 5).

There are a number of advantages with RhD genotyping by this PCR method. Firstly, PCR using DNA enables the RhD genotype of an individual to be unambiguously known. Prenatal counselling often involves prediction of fetal Rh type and a precise RhD genotype would allow accurate predictions of fetal RhD status to be made and advised. Other applications of RhD PCR genotyping exist in Rh paternity testing and in family and genetic studies using Rh as an inheritance marker.

Secondly, unlike serology, the RhD PCR method does not require red blood cells or large quantities of human tissue. In the case of fetal Rh vesting this could lead to safer testing, avoiding the need for percutaneous umbilical blood sampling (PUBS) and the attendant risks of immunisation. RhD PCR typing of a fetus would even be possible using any fetal cell containing DNA such as chorionic villi biopsy or even fetal-derived white blood cells circulating peripherally in the pregnant mother. Another application exists in forensic investigations where materials such as hair, teeth, seminal fluid, or dried blood could potentially be used, virtually independent of age, quantity, and quality.

However, it will be appreciated that none of the prior art referred to above allows a direct determination of whether an RhD positive individual carries 0, 1 or 2 D genes per cell. In regard to previous serological agglutination tests the only information that could be obtained was whether the cells were positive or negative.

The crucial feature of the present invention is that the CE gene can serve as a control and (a) provides a reference point for quantitative D gene measurement and (b) ensures that the PCR for the assay has worked because of the presence of the CE gene as internal control.

Another point of relevance to the present invention is that both D gene and the CE gene are amplified in a single tube PCR.

The invention may also include within its scope a test system or kit for carrying out the above PCR assay. Such kit may include (i) the first gene (e.g. CE gene) as control,
(ii) primers described above,
(iii) buffers as described above,
(iv) polymerase as described above, and
(v) dNTPs as described above, and optionally
(vi) three additional controls with the second gene in zero, single and double doses.

Such a kit in a preferred form may be prepared as described below.

Samples of 100 ng of DNA were obtained from (i) a human subject who is RhD negative (i.e. 0 copy number per cell), (ii) a human subject who was RhD positive but had a copy number of 1 D gene per cell and (iii) a human subject who was RhD positive but had a copy number of 2 D genes per cell. There was added to samples (i), (ii) and (iii) 2 μl of solution A containing the abovementioned primers and water was added to make up the volume to 10 μl in each tube containing samples (i), (ii) and (iii). A further sample (iv) was obtained containing 100 ng of DNA from the human subject being tested to which was added 2 μl of solution A before the total volume was made up to 10 μl. If necessary and more appropriately, DNA samples from other human subjects being tested could also be obtained.

A solution B was prepared containing buffer, dNTP's, $MgCl_2$ and Taq enzyme and 10 μl of solution B was added to four 0.5 ml PCR tubes. Each tube was also provided with a top layer of 30 μl of mineral oil. Each tube was placed in a thermal cycler and preheated to 80° C. To each of these tubes, 10 μl of each of solutions correspond to Samples (i) to (iv) described above were added whereby each of the solutions penetrated the top layer of mineral oil by use of a pipette. The normal cycling procedure involved the following protocol:

|  |  |  |
|---|---|---|
|  | 94° C. | 3 min |
|  | 56° C. | 2 min |
|  | 72° C. | 2 min |
| 32 × | 95° C. | 30 sec |
|  | 65° C. | 45 sec |
|  | 65° C. | 3 min |

From the procedure described above it will be appreciated that a commercial kit could be marketed so as to carry out the detection method of the invention including:

(i) a solution of appropriate primers;
(ii) a solution of buffer, dNTP's, $MgCl_2$ and Taq enzyme;
(iii) reference standards comprising
 (a) a DNA cell extract from one individual indicating the presence of the CE gene in a copy number of least 1 per cell only—(e.g. having one CE band and no band present for the D gene);
 (b) a DNA cell extract from another individual indicating the presence of the CE gene in a copy number of at least 1 per cell as well as the presence of the D gene in a copy number of 1 per cell (e.g. having one CE band and one band present indicating that the individual is RhD positive but of sufficient intensity relative to the CE bard to indicate the D gene is present in a copy number of 1 gene per cell;
 (c) a DNA cell extract from another individual indicating the present of the CE gene in a copy number of at least 1 per cell as well as the presence of the D gene in a copy number of 2 per cell (e.g. having one CE band and another band present indicating that the individual is RhD positive but of sufficient intensity relative to the CE band to indicate that the D gene is present in a copy number of 2 genes per cell).

In the above the word "solution" means each of the respective components are present in the same solution or in different solutions.

Thus when a DNA cell extract is obtained from a patient and if the CE band is amplified but nothing else it will be clear that the patient is RhD negative. If results are obtained corresponding to reference standard (b) or (c) then very quickly not only can the patient by provided with an RhD positive status but the copy number relevant to the D gene can also be readily determined.

The invention may also include within its scope the specific primers referred to above in the experimental section.

In relation to D variants there are two types which are currently known. The first type involves a lesion in the genome which gives a reduced expression of a normal D antigen (termed "weak D"). It is not known how many different types of "lesions" may exist within this type. The second type involves a structural defect on the D antigen which results in part of the D antigen sites or epitopes not being expressed (termed "partial D"). There are at least six categories of the "partial D" and they are categorised as DII, III, IVa, IVb, Va, Vc, VI and VII.

References which discuss these categories are—Lomas et al. *Vox Sang* 1989:57 261–264 Lomas et al. Transfusion 1993 33 535 and Gorick et al. Vox Sang 1993 65 136–140. All the variant forms within these types could be tested by the PCR single tube assay of the invention once it is known what DNA sequence variations are responsible for each respective variant. Targeted primers could then be made. The CE gene would serve as an internal control to validate the PCR and also as a reference to determine the gene copy number for the D gene. A possible combination of gene copies is indicated in Table 2.

The D variant is really an altered and uncommon form of the D gene. However, it can be of clinical significance.

The abovementioned kit could have application in the following areas of transfusion medicine and immunoaematology (a) Ante-Natal Counselling clinics: The kit would be used for precise D gene measurement of husbands of Rh D negative wives, especially those sensitized to the D gene from a prior pregnancy.

(b) Blood Grouping Reference Laboratories: The kit determines the precise D gene level and therefore, in combination the Cc and Ee serology typing results allows a determination of the precise genotype. As an example of how this can be done, reference should be made to Table 1 which tabulates the classifications that were obtained by D gene measurement on 102 donors versus the serological predictions. Reference should be made to the corrected genotype which was required in 5 cases and this was on a fairly homogenous and well tested blood donor population. Serological predictors are highly dependent on race origin.

(c) Laboratories involved in paternity testing in which precise Rh CDE haplotype combinations are required for putative family members.

(d) Forensic laboratories: The PCR assay can be done on blood, hair or other body tissue (please note the assay is at this stage only quantitative for purified DNA).

(e) Transfusion Medicine: In cases of massive transfusions before a patients blood group was performed: in such cases Rh PCR DNA testing could be the only way a blood group could be obtained—PCR for Cc and Ee would also be needed for this.

(f) The inability to quantify the number of Rh D genes present means that a true Rh D genotype of an individual could not be assigned.

Reference may also be made to (a) Hyland et al., in Blood, Vol 83, No 2 Jan. 15) 1994 566–572 and (b) Hyland at al., Blood Vol 84, (1994) which references are also concerned with RhD genotyping using PCR whereby the abovementioned PCR method of the present invention was validated in relation to the D gene dosages. In references (a) and (b) the assumption that the D gene is not present in RhD negative cases was tested by appropriate screening of RhD negative individuals. It was ascertained that this assumption does not always hold true but nevertheless the accuracy of the detection method of the invention is over 99%. On rare occasions false positive results may arise. This will occur for less than 0.5% for all RhD negative cases. False negative results may occur for the very rare RD variants e.g. DIV and V variants which occur in less then 0.4% of the population. Furthermore the clinical significance of these variants is minimal.

It will also be readily apparent that the method of the invention may also be applied to exon 10 and exon 4 to 5 of the RhD gene if desired.

The invention also includes within its scope the reference standards per se.

TABLE 1

RhD gene measurements among 102 blood donors
Comparison of predicted versus observed D gene levels

| Serological prediction | no. | Concordant D genotype | Corrected Genotype |
|---|---|---|---|
| CDe/ce | 35 | 32 | 3 CDe/cDe |
| CDe/CDe | 20 | 19 | 1 CDe/Ce |
| cDE/ce | 14 | 14 | |
| ce/ce | 14 | 14 | |
| CDe/cDE | 14 | 14 | |
| cDE/cDE | 3 | 2 | 1 cDE/cE |
| Ce/cE | 1 | 1 | |
| cDe/ce | 1 | 1 | |
| TOTAL | 102 | 95% | |

RFLPs determined from Southern analysis using 5' and 3' Rh probes

TABLE 2

| CF | normal D | Variant D (any one of) |
|---|---|---|
| 2 | 0 | 0 |
| 2 | 1 | 0 |
| 2 | 2 | 0 |
| 2 | 0 | 1 |
| 2 | 1 | 1 |
| 2 | 0 | 2* |

*most likely

We claim:

1. A process for detecting and quantifying the presence in copy number of one of a number of closely related genes, wherein said process comprises:

(i) carrying out a PCR assay with one or more test samples from a human or animal cell extract wherein in a single tube each sample includes a DNA cell extract having (a) a first gene always present in such DNA cell extracts at a fixed copy number of 1 or more per cell, whereby said first gene functions as an internal control, and (b) a second gene closely related to the first gene but usually present in the DNA cell extract in a copy number of 0, 1, 2 or more per cell, together with a first primer specific for said first gene, a second primer specific for said second gene and a third primer common to both the first gene and the second gene to produce a first PCR product corresponding to the first gene which first PCR product generates a first signal and, if the second gene is present, a second PCR product corresponding to the second gene which second PCR product generates a second signal, whereby said first and second PCR products are produced by said first, second and third primers; and (ii) quantifying the presence in copy number of the second gene in each test sample by comparison of the first signal with the second signal.

2. A process as claimed in claim 1, wherein in step (i), a plurality of different reference standards are used, each comprising a DNA cell extract indicating the presence of said first gene in a copy number of at least 1 per cell and indicating the presence of the second gene in a copy number of 0, 1, 2 or more per cell, wherein the number of reference standards corresponds to the variation in copy number of the second gene; wherein said PCR assay is also carried out with said reference standards to detect and determine the presence in copy number of said second gene.

3. A process as claimed in claim 2, wherein said plurality of reference standards comprises:
   (a) said first gene and said second gene in a copy number of 0;
   (b) said first gene and said second gene in a copy number of 1; and
   (c) said first gene and said second gene in a copy number of 2.

4. A process as claimed in claim 1 used for RhD genotyping wherein the first gene corresponds to the RhCcEe gene and the second gene corresponds to the RhD gene or an RhD gene variant.

5. A process as claimed in claim 1 wherein the first primer is (SEQ ID NO: 4) 5'-GATTACGAATTCCATTGCCGTTCCAGACA-3' the second primer is (SEQ ID NO: 3) 5'-TACCAGATTACGAATTCATGCCATTGCCGGCTC-3' and the third primer is (SEQ ID NO: 2) 5'-GATTACGAATTCGTAACCGAGTGCTGGGGATT-3'.

6. A test kit for detection and quantification in copy number of one of a number of closely related genes by PCR assay with one or more test samples from a human or animal cell extract, which kit comprises
   a plurality of reference standards each comprising a DNA cell extract having a RhCcEe gene which is always present in DNA cell extracts from said human or animal cells at a fixed copy number of at least one per cell, whereby said RhCcEe gene functions as an internal control, and a RhD gene closely related to said RhCcEe gene but usually present in said DNA cell extract in a copy number of 0, 1, 2 or more per cell, wherein the number of said reference standards corresponds to the variation in copy number of said second gene, and a set of primers comprising a first primer specific for said first gene, a second primer specific for said second gene, and a third primer common to both the first gene and the second gene for use in producing a first PCR product corresponding to the RhCcEe gene which first PCR product generates a first signal and, if the RhD gene is present, for use in producing a second PCR product corresponding to the RhD gene which second PCR product generates a second signal, wherein said PCR assay for each test sample is performed in a single tube.

7. A test kit as claimed in claim 6, wherein the reference standards include:
   (a) a DNA cell extract indicating the presence of the RhCcEe gene in a copy number of at least 1 per cell but excluding the presence of the RhD gene; and
   (b) a DNA cell extract indicating the presence of the RhCcEe gene in a copy number of at least 1 per cell as well as the presence of the RhD gene in a copy number of 1 per cell.

8. A test kit as claimed in claim 7, wherein there is included a further reference standard comprising a DNA cell extract indicating the presence of the RhCcEe gene in a copy number of least 1 per cell as well as the presence of the RhD gene in a copy number of 2 per cell.

9. A test kit as claimed in claim 6, wherein the reference standards include:
   (a) a DNA cell extract from one individual indicating the presence of the RhCcEe gene in a copy number of at least 1 per cell but excluding the presence of the RhD gene;
   (b) a DNA cell extract from another individual indicating the presence of the RhCcEe gene in a copy number of at least 1 per cell as well as the presence of the RhD gene in a copy number of 1 per cell; and
   (c) a DNA cell extract indicating the presence of the RhCcEe gene in a copy number of least 1 per cell as well as the presence of the RhD gene in a copy number of 2 per cell.

10. A set of reference standards for inclusion in a kit as claimed in claim 6 comprising:
    (a) a DNA cell extract having a RhCcEe gene present at a fixed copy number of 1 or more per cell and having a RhD gene closely related to the first gene and present at a copy number of 2 per cell;
    (b) a DNA cell extract having a RCcEe gene present at said fixed copy number and having a RhD gene present at a copy number of 1 per cell; and
    (c) a DNA cell extract having a RhCcEe gene present at said fixed copy number and having a RhD gene present at a copy number of 0 per cell.

* * * * *